(12) United States Patent
Wald

(10) Patent No.: US 6,573,103 B1
(45) Date of Patent: Jun. 3, 2003

(54) ANTENATAL SCREENING FOR DOWN'S SYNDROME

(76) Inventor: Nicholas J Wald, 22 Staverton Road, Oxford, OX2 6XJ (GB)

( * ) Notice: Subject to any disclaimer, the term of this patent is extended or adjusted under 35 U.S.C. 154(b) by 0 days.

(21) Appl. No.: 09/301,621

(22) Filed: Apr. 29, 1999

(30) Foreign Application Priority Data

Apr. 29, 1998 (GB) .............................................. 9809209
Jun. 26, 1998 (GB) .............................................. 9813905

(51) Int. Cl.⁷ .............................................. G01N 33/48
(52) U.S. Cl. .......................... 436/65; 436/86; 436/814; 436/818; 436/510; 435/4
(58) Field of Search .............................. 436/65, 86, 87, 436/817, 814, 818, 510, 4; 435/7.1, 7.4, 21, 4

(56) References Cited

U.S. PATENT DOCUMENTS

| | | |
|---|---|---|
| 4,874,693 A | 10/1989 | Bogart |
| 5,258,907 A | 11/1993 | Macri |
| 5,316,953 A | 5/1994 | Macri |
| 5,506,150 A | 4/1996 | Canick et al. |

FOREIGN PATENT DOCUMENTS

| | | |
|---|---|---|
| EP | 0617921 | 3/1993 |
| WO | WO 90/08325 | 7/1990 |
| WO | WO 94/12884 | 6/1994 |
| WO | WO 94/21686 | 9/1994 |
| WO | WO 95/32431 | 11/1995 |
| WO | WO 97/03363 | 1/1997 |

OTHER PUBLICATIONS

Kennard et al: "Antenatal Screening for Down's Syndrome," *J. Med Screen* 4, 181–246, 1997.
Cuckle et al: "Maternal Serum Screening for Down's Syndrome in Early Pregnancy," *BMJ* 297,883–887, 1998.
Royston et al: "Model–Based Screening by Risk With Application to Down's Syndrome," *Stat Med* 11, 256–268.
Hackshaw: (1997) "Combining Ultrasound and Biochemistry in First–Trimester Screen for Down's Syndrome," *Prenat Diagn* 17, 821–829.
Densem et al: (1996) "Prenatal Screening for Down's Syndrome Using Inhibit–A as a Serum Marker," *Prenat Diagn* 16, 143–153.
Densem et al: (1997) "Inhibin–A in Down's Syndrome Pregnancies; Revised Estimate of Standard Deviation," *Prenat Diagn* 17, 285–290.
Watt et al: (1998); "The Pattern of Maternal Serum Inhibin–A concentrations in the Second Trimester of Pregnancy," *Prenat Diagn* 18, 846–848.
Cuckle et al (1987): Estimating a Woman's Risk of Having a Pregnancy Associated with Down's Syndrome Using Her Age and Serum Alpha–Foetoprotein Level, *Br J Obstet Gynaecol* 94, 387–402.

Wald et al Annals of Medicine vol. 26, No. 1, Jan. 1994 pp. 23–29 "First Trimester Biochemical Screening for Down's Syndrome", 1994.
Wald N J, Watt H C and Hackshaw A K, "Integrated Screening For Down's Syndrome Based On Tests Performed During The First And Second Trimesters", New England Medical Journal of Medicine 1999; 341:461–76.
Herman A, Weinraub Z, Dreazen E, Arieli S, Rozansky S, Bukovsky I and Maymon R, "Combined first trimester nuchal translucency and second trimester biochemical screening tests among normal pregnancies", Prenatal Diagnosis 2000; 20: 781–784.
Hyett and Thilaganathan, "First trimester screening for fetal abnormalities", Current Opinion in Obstetrics and Gynecology 1999; 11: 563–569.
Nicolaides, Heath and Liao, "The 11–14 week scan", Balliere's Clinical Obstetrics and Gynaecology, vol. 14, No. 4, pp. 581–594, 2000.
"Noninvasive screening for aneuploidy: who, when, and why?", Contemporary Ob/Gyn, Feb. 2000, pp. 76–104.
"Integrated Test", DSNEWS 2000, vol. 7, Issue 2, pp 28–29.
Campogrande M, Viora E, Errante G, Bastonero S, Sciarrone A, Grassi Pirrone P, Perona M, Mancini G, Dall'Amico D, Pavanello E, Guaraldo V, "Correlations between first and second trimester markers for Down's syndrome screening", J. Med Screen 2001; 8:163–164.
Gilbert, Augood, Gupta, Ades, Logan, Sculpher and van der Meulen, "Screening for Down's syndrome: effects, safety, and cost effectiveness of first and second trimester strategies", BMJ 2001; 323: Aug. 25, 2001.
Lam, Lee, Sin, Wong and Tang, "First–trimester nuchal translucency and second–trimester serum screening for fetal Down's syndrome", Ultrasound Obstet Gynecol 12 (Suppl 1): A62, Nov., 1998.
Lam, Tang, Lee, Sin, Tang, Wong and Wong, "Acceptability of serum screening as an alternative to cytogenetic diagnosis of Down syndrome among women 35 years or older in Hong Kong", Prenatal Diagnosis 2000; 20: 487–490.
Thilaganathan et al, Ultrasonic Obstet. Gynecol. 10 (1997) 261–264.

*Primary Examiner*—Lyle A. Alexander
(74) *Attorney, Agent, or Firm*—Nixon & Vanderhye, P.C.

(57) ABSTRACT

A method of screening for fetal Down's syndrome is described. Screening marker levels are measured. These may be measurements of a biochemical marker in a maternal sample or measurements of a marker from an ultrasound scan. The marker levels are used to calculate a risk of Down's syndrome. Instead of using markers from a single stage of pregnancy, the method uses markers from two or more different stages of pregnancy, typically one being in the first and another being in second trimester. The method may be automated.

24 Claims, 6 Drawing Sheets

ANTENATAL SCREENING FOR DOWN'S SYNDROME

BACKGROUND OF THE INVENTION

This invention relates to a method and apparatus for determining for screening purposes whether a pregnant woman is at an increased risk of fetal Down's syndrome.

The risk of Down's syndrome in a fetus is known to increase with the age of the mother. In addition, abnormally high or low concentrations of certain substances in the maternal serum (biochemical markers), and abnormally large or small measurements of certain ultrasonographic signs (ultrasound markers), are known to be associated with an increased risk of Down's syndrome in the fetus.

Information on one or more of these biochemical or ultrasound markers (collectively called screening markers) can be combined with the age-related risk of Down's syndrome, to form the basis of a screening test.

The aim of a screening test is to identify women who are at a sufficiently high risk of Down's syndrome to justify a further test which is diagnostic of Down's syndrome. Such further diagnostic tests, eg. chorionic villus sampling or amniocentesis, involve sampling procedures that carry a certain risk to the mother and/or fetus, the induction of miscarriage and fetal limb defects being among the recognised hazards. There is, therefore, a need for screening tests that maximise the chance of identifying those pregnancies at highest risk of Down's syndrome, so as to justify further diagnostic tests with their attendant risks.

The effectiveness of a screening test depends on its ability to discriminate between pregnancies with Down's syndrome and unaffected pregnancies. The discriminatory power of a test is usually specified in terms of the detection rate achieved for a given false-positive rate, or in terms of the false-positive rate required to achieve a given detection rate. The detection rate is the proportion of Down's syndrome pregnancies with a positive result. The false-positive rate is the proportion of unaffected pregnancies with a positive result.

Different screening markers generally impart more discriminatory power to a screening test at one stage of the pregnancy than at other stages. Currently employed screening tests rely on certain combinations of biochemical and ultrasound markers that have been identified as being effective when used together at a specific, single stage of pregnancy.

For example, the "combined test" carried out in the first trimester using nuchal translucency and free β-hCG and PAPP-A as screening markers can achieve an 80% detection rate with a 5% false-positive rate. The "triple test" carried out in the second trimester uses AFT, $uE_3$ and hCG as screening markers. The "quadruple test" carried out in the second trimester uses the screening markers of the "triple test" plus inhibin-A. The "triple test" and "quadruple test" can achieve an 80% detection rate with a false positive rate of 10% and 6.6% respectively. However, a screening test with greater discriminatory power would be desirable. A high false-positive rate means that a large number of women with screen-positive results in fact have unaffected pregnancies. For these unaffected women the screen-positive result, quite apart from causing considerable anxiety, might lead to a diagnostic procedure such as amniocentesis or chorionic villus sampling which have a risk of miscarriage of about 1 in 100.

An object of the present invention is to derive a screening test which has an improved discriminatory power over the known tests.

Further objects of the invention are to produce an apparatus and a computer program product for implementing the screening test.

BRIEF SUMMARY OF THE INVENTION

The present invention, however, relies on screening markers obtained from two or more different stages of pregnancy. In particular, according to the first aspect of the present invention there is provided a method of determining a pregnant woman's risk of having a fetus with Down's syndrome, the method comprising the steps of:

measuring at least one screening marker level from a first stage of pregnancy by:
  (i) assaying a sample obtained from the pregnant woman at said first stage of pregnancy for at least one biochemical screening marker; and/or
  (ii) measuring at least one screening marker from an ultrasound scan taken at said first stage of pregnancy;

measuring at least one screening marker level from a second stage of pregnancy by:
  (i) assaying a sample obtained from the pregnant woman at said second stage of pregnancy for at least one biochemical screening marker; and/or
  (ii) measuring at least one screening marker from an ultrasound scan taken at said second stage of pregnancy; and determining the risk of Down's syndrome using the measured screening marker levels from both the first and second stages of pregnancy.

The risk of Down's syndrome may be determined from the marker levels by a statistical analysis based on reference data which may be derived from existing or future studies. Preferably the step of determining the risk of Down's syndrome comprises deriving the likelihood ratio of Down's syndrome using a multivariate analysis based on distribution parameters derived from a set of reference data.

Such a method can provide a single integrated screening test that is more effective at identifying affected pregnancies than tests which are based on samples collected at a single stage of pregnancy, that is it yields a higher detection rate at the same false-positive rate or a lower false-positive rate at the same detection rate. For example if the risk of Down's syndrome is determined by a method integrating nuchal translucency measurements and PAPP-A in the first trimester and the "quadruple test" using AFP, $uE_3$ hCG and inhibin-A as markers in the second trimester, it is estimated that at a detection rate of 80%, the false-positive rate is brought below 1%. This is a considerable improvement over the 5% false positive rate for the "combined test". This means fewer unaffected pregnancies will be classified as screen-positive. Furthermore, at an 80% detection rate, if the expense of the additional screening measurements amounts to, say, US$100 there would be no overall extra expense because the extra screening costs would be offset by savings from performing substantially fewer invasive diagnostic tests.

The present invention utilises the fact that the ability of different screening markers to discriminate between Down's syndrome pregnancies and unaffected pregnancies varies according to the stage of pregnancy. For example, the screening marker PAPP-A is most useful before 14 weeks, but not afterwards, and vice versa with the screening marker inhibin-A, as summarised in Wald N J, Kennard A, Hackshaw A, McGuire A. (1997); Antenatal screening for Down's syndrome. J Med Screen 4,181–246.

The present invention can also provide the important advantage of permitting the use of the maternal serum AFP for screening for open neural tube defects (which is best done after 15 weeks of pregnancy) as well as using the earlier test results for Down's syndrome screening.

According to a second aspect of the present invention, there is provided a method of determining a pregnant woman's risk of having a fetus with Down's syndrome, the method comprising the steps of:

measuring at least one screening marker level from a first stage of pregnancy by:
(i) assaying a sample obtained from the pregnant woman at said first stage of pregnancy for at least one biochemical screening marker; and/or
(ii) measuring at least one screening marker from an ultrasound scan taken at said first stage of pregnancy;

determining a first risk estimate of Down's syndrome using the measured screening marker levels from the first stage of pregnancy; comparing the first risk estimate with a predetermined cut-off level to initially classify the pregnant woman as screen-positive or screen-negative based on the comparison; and if the pregnant woman is initially classified as screen-negative: measuring at least one screening marker level from a second stage of pregnancy by:
(i) assaying a sample obtained from the pregnant woman at said second stage of pregnancy for at least one biochemical screening marker; and/or
(ii) measuring at least one screening marker from an ultrasound scan taken at said second stage of pregnancy; and determining the risk of Down's syndrome using the measured screening marker levels from second stage of pregnancy.

The processing of the measurements of the screening marker levels may be implemented by an appropriately programmed computer. In another implementation, these computer-implemented steps may be provided as an article of manufacture, that is, in accordance with a third aspect of the present invention, a computer program storage medium readable by a computing system and encoding a computer program of instructions for executing a computer process for determining a pregnant woman's risk of having a fetus with Down's syndrome, said computer process comprising the steps of:

inputting a measurement of at least one screening marker level from a first stage of pregnancy obtained by:
(i) assaying a sample obtained from the pregnant woman at said first stage of pregnancy for at least one biochemical screening marker; and/or
(ii) measuring at least one screening marker from an ultrasound scan taken at said first stage of pregnancy;

inputting a measurement of at least one screening marker level from a second stage of pregnancy obtained by
(i) assaying a sample obtained from the pregnant woman at said second stage of pregnancy for at least one biochemical screening marker; and/or
(ii) measuring at least one screening marker from an ultrasound scan taken at said second stage of pregnancy; and determining the risk of Down's syndrome using the input screening marker levels from both the first and second stages of pregnancy.

The computer-implemented steps may also be provided as a machine including modules for performing the processing, that is, in accordance with a fourth aspect of the invention, an apparatus for determining a pregnant woman's risk of having a fetus with Down's syndrome, the apparatus comprising:

data input means for inputting a measurement of at least one screening marker level from a first stage of pregnancy obtained by:
(i) assaying a sample obtained from the pregnant woman at said first stage of pregnancy for at least one biochemical screening marker; and/or
(ii) measuring at least one screening marker from an ultrasound scan taken at said first stage of pregnancy;

data input means for inputting a measurement of at least one screening marker level from a second stage of pregnancy obtained by
(i) assaying a sample obtained from the pregnant woman at said second stage of pregnancy for at least one biochemical screening marker; and/or
(ii) measuring at least one screening marker from an ultrasound scan taken at said second stage of pregnancy; and calculation means for determining the risk of Down's syndrome using the input screening marker levels from both the first and second stages of pregnancy.

BRIEF DESCRIPTION OF THE DRAWINGS

To allow better understanding the following description of a method and apparatus for screening for fetal Down's syndrome according to the present invention is given by way of non-limitative example with reference to the drawings in which.

DETAILED DESCRIPTION

Figure 1:
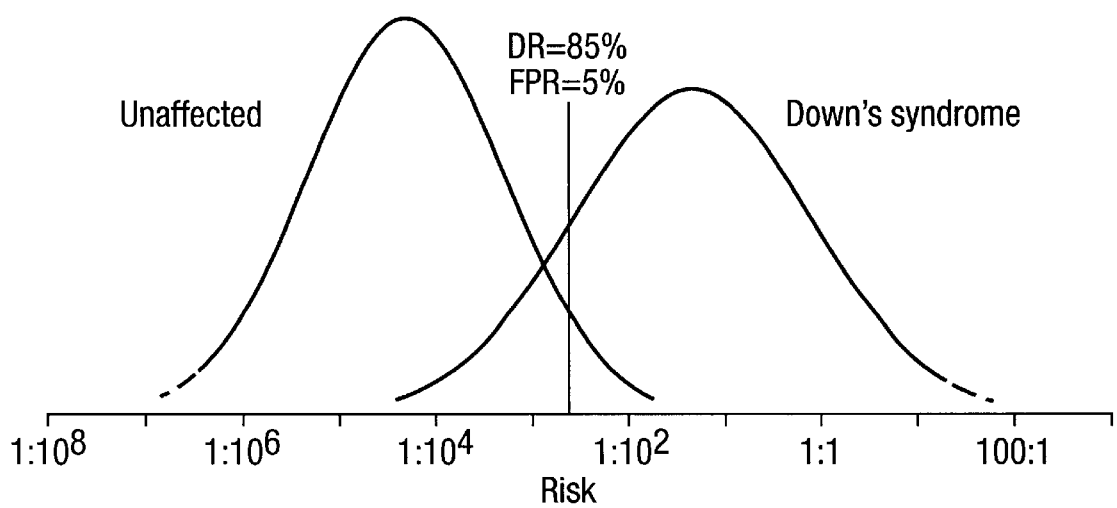
FIGS. 1, 2, 3 and 4 show the distributions of risk in (a) Down's syndrome and (b) unaffected pregnancies using different sets of markers at two stages in pregnancy.

Measurements carried out on biochemical samples may include assaying one or more of the following biochemical markers of Down's syndrome in maternal serum or plasma, among others:

alpha feto-protein (AFP)
unconjugated oestriol ($uE_3$)
human chorionic gonadotrophin (hCG)
free alpha sub-unit of hCG (free α-hCG)
free beta sub-unit of hCG (free β-hCG)
inhibin, preferably dimeric inhibin-A (inhibin A)
pregnancy-associated plasma protein A (PAPP-A)

Measurements carried out on biochemical samples may also include assaying one or more of the following biochemical markers of Down's syndrome in maternal urine, among others:

beta-core hCG total oestriol

Measurements carried out on ultrasound images may include one or more of the following ultrasound markers of Down's syndrome, among others:

nuchal translucency (NT) thickness, nuchal fold thickness femur length humerus length hyperechogenic bowel renal pyelectasis fetal heart rate certain cardiac abnormalities Use of the above and other screening markers at a single stage of pregnancy is known, so the specific techniques by which measurements are obtained need not be described in detail here. In the known methods the biochemical and ultrasound markers levels are interpreted in combination with maternal age, to derive a risk estimate. The estimation of risk is conducted using standard statistical techniques. For example, known methods are described in Wald N J, Cuckle H S, Densem J W, et al (1988); Maternal serum screening for Down's syndrome in early pregnancy. BMJ 297, 883–887 and in Royston P, Thompson S G (1992); Model-based screening by risk with application to Down's syndrome. Stat Med 11, 256–268.

In the present method, a single risk estimate is derived from measurements of marker levels carried out on biochemical samples (eg. serum or plasma or urine or cells) and/or ultrasound images which are obtained sequentially at two or more different stages of pregnancy. Thus the calculation can be integrated as a single test at one stage. The individual measurements are obtained by using known methods. One or more screening markers from each of the stages of pregnancy may be used. Any markers which are effective at each particular stage may be selected. For example, in one embodiment of this invention, the markers from the first trimester between 8 to 13 weeks of pregnancy are the "combined test" markers (NT free β-hcG and PAPP-A) and the markers from the second trimester between 14 to 22 weeks are the "quadruple test" markers AFP, $uE_3$, total hCG and inhibin-A. Preferably, one would not use both free β-hcG from the first trimester because of an expected high correlation between these markers. Therefore the preferred embodiment is to use NT and PAPP-A from the first trimester and the "quadruple test" markers from the second trimester. Other possible marker combinations are set out in Table 4a and 4b below. In practice one might need to omit the use of NT at some test centres which are not experienced in its measurement or to omit the use of inhibin-A at some test centres which prefer to retain their current use of the "triple test" markers instead of the "quadruple test" markers.

The measured marker levels are used in combination, preferably together with maternal age, to derive a risk estimate of having an affected pregnancy.

Most screening markers levels are known to vary with gestational age. To take account of this variation each marker level may be expressed as a multiple of the median level (MoM) for unaffected pregnancies of the same gestational age. Especially, for markers derived from ultrasound scans, crown-rump length (CRL) or biparietal diameter (BPD) measurement are alternative measures of gestational age. MoMs may be adjusted in a known way to take account of factors which are known to affect marker levels, such as maternal weight, ethnic group, diabetic status and the number of fetuses carried.

When using several markers in combination to screen for a particular disorder, it is desirable to take account of correlation between the markers. If two markers are perfectly correlated, one adds nothing to the other in assessing the risk of having the disorder, whereas if they are completely uncorrelated, each provides an independent measure of risk. To the extent that they may be partially correlated, each will provide some independent information. The correlations between markers known to be suitable for use at the same stage of pregnancy are known, for example as summarised in Table 1 below for the preferred markers.

In the present method, the markers from different stages of pregnancy are assumed to be independent of each other among affected and unaffected pregnancies. There may be some degree of correlation between these markers but this is unlikely to have a material effect on the estimated screening performances. In any case, if required, such correlation coefficients can be incorporated into the calculation of risk estimates in the same way as correlation coefficients are already used in the present method.

Calculation of risk from the measured marker levels is based on the observed relative frequency distribution of marker level in (a) Down's syndrome and (b) unaffected pregnancies. Any of the known statistical techniques may be used. Preferably the multivariate Gaussian model is used, which is appropriate where the observed distributions are reasonably Gaussian. Such multivariate Gaussian analysis is in itself known, for example from Wald N J, Cuckle H S, Densem J W, et al (1988) and Royston P, Thompson S G (1992) referred to above. Thus no detailed discussion is necessary, but a summary is given as follows.

If a matrix representation is used, the height H of the Gaussian distribution for a given set of measured levels is given by the equation:

$$H = \frac{1}{\prod(\sigma) \cdot (2\pi)^{p/2} \cdot det(R)^{1/2}} \exp(-1/2 \cdot Z^T \cdot R^{-1} \cdot Z)$$

where p is the number of markers, $\Pi(\sigma)$ is the product of the standard deviations for each distribution, Z is a matrix containing the measured level of each marker expressed in standard deviation units, namely ((measured level—mean)/standard deviation), and R is a matrix containing the correlations between the tests.

For each test two Gaussian heights are calculated, (a) one for the Down's syndrome distribution and (b) the other for the unaffected distribution. For this calculation the necessary statistical distribution parameters which specify the Gaussian distribution are the mean, standard deviation and correlations for the two distributions. These are known, being derivable from observed distributions and are given for some markers for example in Wald N J, Hackshaw A K (1997); Combining ultrasound and biochemistry in first-trimester screening for Down's syndrome. Prenat Diagn 17, 821–829; in Wald N J, Densem J W, George L, Muttukrishna S, Knight P G (1996); Prenatal screening for Down's syndrome using inhibin-A as a serum marker. Prenat Diagn 16, 143–153; and in Wald N J, Densem J W, George L, Muttukrishna S, Knight P G (1997) Inhibin-A in Down's syndrome pregnancies: revised estimate of standard deviation. Prenat Diagn 17, 285–290, as summarised in Table 1 below for the preferred markers. The distribution parameters are stored as reference data for use in the analysis.

Table 1: Standard deviations, correlation coefficients, and means ($\log_{10}$ MoM) for unaffected and Down's syndrome pregnancies for screening markers (based on the gestational age estimate using an ultrasound scan examination, with maternal weight adjustment of serum markers).

|  | Unaffected pregnancies | Down's syndrome pregnancies |
|---|---|---|
| STANDARD DEVIATIONS | | |
| Nuchal translucency | 0.1717 | 0.2396 |
| PAPP-A | 0.2659 | 0.3471 |
| Free β-hCG | 0.2833 | 0.2870 |
| AFP | 0.1789 | 0.1821 |
| $uE_3$ | 0.1102 | 0.1210 |
| Total hCG | 0.2239 | 0.2520 |
| Inhibin-A | 0.2154 | 0.1986 |
| CORRELATION COEFFICIENTS | | |
| Nuchal translucency — PAPP-A | 0.0000 | 0.0000 |
| PAPP-A — Free-β-hCG | 0.1407 | 0.0648 |
| Free β-hCG — Nuchal translucency | 0.0000 | 0.0000 |
| AFP — $uE_3$ | 0.0901 | 0.1770 |
| AFP — Total hCG | 0.0596 | 0.2148 |
| AFP — Inhibin-A | 0.0780 | 0.1045 |
| $uE_3$ — Total hCG | −0.0586 | −0.0474 |
| $uE_3$ — Inhibin-A | 0.0175 | −0.1024 |
| Total hCG — Inhibin-A | 0.1882 | 0.2493 |
| MEANS | | |
| Nuchal translucency | 0.0000 | 0.3118 |
| PAPP-A | 0.0000 | −0.3704 |
| Free β-hCG | 0.0000 | 0.2540 |
| AFP | 0.0000 | −0.1427 |
| $uE_3$ | 0.0000 | −0.1411 |
| Total hCG | 0.0000 | 0.3023 |
| Inhibin-A | 0.0000 | 0.2522 |

The ratio of the two Gaussian heights gives the likelihood ratio. The likelihood ratio is a measure of the increased risk of having a disorder, given a particular combination of test results, compared to the background risk (that is, the risk in the absence of the test results).

The likelihood ratio is multiplied by the known background risk, which is preferably the age-specific risk, to calculate the improved estimate of risk. The age-specific risk can be calculated using the maternal age distribution of England and Wales for 1984–1988 (taken from Office of Population Censuses and Surveys (1985–1990); Birth Statistics, Series EM1, Nos, 11, 12, 15–17, London: HMSO) and the birth rate of Down's syndrome in live births (taken from Cuckle H S, Wald N J, Thompson S G (1987); Estimating a woman's risk of having a pregnancy associated with Down's syndrome using her age and serum alpha-fetoprotein level, Br J Obstet Gynaecol 94, 387–402).

The estimated risk is classified as screen-positive or screen-negative based on a comparison with a predetermined cut-off. The value of the cut-off may be altered to vary the detection rate and false-positive rate.

Expected Down's syndrome detection rates and false-positive rates using the present invention have been estimated. They show an improved performance over the tests from a single stage of pregnancy. Tables 2, 3 and 4 illustrate this improved performance. Performance is shown in tables 2a, 3a and 4a in terms of the detection rate achieved at specified false-positive rates and in tables 2b, 3b and 4b in terms of the false-positive rate achieved at specified detection rates. The estimates are based on a gestational age estimate using an ultrasound scan, with maternal weight adjustment of serum markers. Tables 2a and 2b show the performance of different screening tests currently performed between 10 and 13 weeks of pregnancy. Tables 3a and 3b show the performance of different screening tests currently performed between 14 and 22 weeks of pregnancy. Tables 4a and 4b show the performance of four different integrated screening tests according to the present invention. Tables 5a and 5b show the performance of the preferred embodiment (using NT and PAPP-A from the first trimester and the "quadruple test" markers from the second trimester) and also with the omission of inhibin-A, NT and both.

The performance of the integrated tests of the present method can be seen to be superior, because at each false-positive rate the detection rate of the present method is higher than that of each currently available tests based on a single stage of pregnancy, and at each detection rate the false-positive rate of the present method is lower than that of the currently available tests. As shown in Tables 5a and 5b even omitting inhibin-A, NT or both, it is of benefit to integrate the markers from the first and second trimesters into a single screening test.

TABLE 2a

| | Detection rate (%). Maternal age with: | | | |
|---|---|---|---|---|
| False positive rate (%) | AFP and total hCG | AFP, $uE_3$ and total hCG | AFP, $uE_3$, free α-hCG and free β-hCG | AFP, $uE_3$, total hCG and inhibin-A |
| 1 | 35 | 46 | 53 | 54 |
| 2 | 44 | 55 | 61 | 64 |
| 3 | 50 | 62 | 66 | 69 |
| 4 | 55 | 66 | 70 | 73 |
| 5 | 59 | 69 | 73 | 76 |

TABLE 2b

| | False-positive rate (%). Maternal age with: | | | |
|---|---|---|---|---|
| Detection rate (%) | AFP and total hCG | AFP, $uE_3$ and total hCG | AFP, $uE_3$, free α-hCG and free β-hCG | AFP, $uE_3$, total hCG and inhibin-A |
| 55 | 4.0 | 1.9 | 1.2 | 1.1 |
| 60 | 5.4 | 2.7 | 1.8 | 1.6 |
| 65 | 7.1 | 3.8 | 2.7 | 2.2 |
| 70 | 9.4 | 5.2 | 4.0 | 3.2 |
| 75 | 12 | 7.3 | 5.9 | 4.5 |
| 80 | 17 | 10 | 8.9 | 6.6 |
| 85 | 22 | 15 | 14 | 9.8 |
| 90 | 30 | 22 | 22 | 15 |
| 95 | 45 | 35 | 37 | 26 |

TABLE 3a

| | Detection rate (%). Maternal age with: | | |
|---|---|---|---|
| False positive rate (%) | NT | Free β-hCG and PAPP-A | NT, free β-hCG and PAPP-A |
| 1 | 43 | 40 | 62 |
| 2 | 51 | 49 | 70 |
| 3 | 56 | 55 | 75 |
| 4 | 59 | 59 | 78 |
| 5 | 63 | 62 | 80 |

TABLE 3b

| Detection rate (%) | False-positive rate (%). Maternal age with: | | |
|---|---|---|---|
| | NT | Free β-hCG and PAPP-A | NT, free β-hCG and PAPP-A |
| 55 | 2.8 | 3.1 | 0.5 |
| 60 | 4.2 | 4.4 | 0.8 |
| 65 | 5.9 | 6.2 | 1.3 |
| 70 | 8.7 | 8.6 | 2.0 |
| 75 | 13 | 12 | 3.1 |
| 80 | 18 | 17 | 5.0 |
| 85 | 26 | 23 | 8.1 |
| 90 | 37 | 34 | 14 |
| 95 | 58 | 51 | 27 |

TABLE 4a

| False positive rate (%) | Detection rate (%). Maternal age with: | | | |
|---|---|---|---|---|
| | At 10–13 weeks: FAPP-A At 14–22 weeks: AFP, uE₃ total hCG and inhibin-A | PAPP-A and free β-hCG AFP, uE₃ and inhibin-A | NT and PAPP-A AFP, uE₃, total hCG and inhibin-A | NT, PAPP-A and free β-hCG AFP, uE₃, and inhibin-A |
| 1 | 66 | 65 | 81 | 80 |
| 2 | 75 | 74 | 86 | 86 |
| 3 | 79 | 78 | 89 | 89 |
| 4 | 82 | 81 | 91 | 91 |
| 5 | 85 | 84 | 92 | 92 |

TABLE 4b

| Detection rate (%) | False-positive rate (%). Maternal age with: | | | |
|---|---|---|---|---|
| | At 10–13 weeks: PAPP-A At 14–22 weeks: AFP, uE₃, total hCG and inhibin-A | PAPP-A and free β-hCG AFP, uE₃ and inhibin-A | NT and PAPP-A AFP, uE₃, total hCG and inhibin-A | NT, PAPP-A and free β-hCG AFP, uE₃, and inhibin-A |
| 55 | 0.4 | 0.4 | 0.1 | 0.1 |
| 60 | 0.6 | 0.6 | 0.1 | 0.1 |
| 65 | 0.9 | 1.0 | 0.2 | 0.2 |
| 70 | 1.4 | 1.5 | 0.3 | 0.3 |
| 75 | 2.1 | 2.3 | 0.5 | 0.6 |
| 80 | 3.2 | 3.5 | 0.9 | 1.0 |
| 85 | 5.1 | 5.6 | 1.7 | 1.9 |
| 90 | 8.8 | 9.5 | 3.4 | 3.7 |
| 95 | 17 | 18 | 8.2 | 8.8 |

TABLE 5a

| False positive rate (%) | Detection Rate (%). Maternal age with: | | | |
|---|---|---|---|---|
| | Preferred embodiment | Omitting inhibin-A | Omitting NT | Omitting NT and inhibin-A |
| 1 | 81 | 76 | 66 | 60 |
| 3 | 89 | 86 | 79 | 74 |
| 5 | 92 | 90 | 85 | 80 |
| 7 | 94 | 92 | 88 | 84 |

TABLE 5b

| Detection rate (%) | False-positive rate (%). Maternal age with: | | | |
|---|---|---|---|---|
| | Preferred embodiment | Omitting inhibin-A | Omitting NT | Omitting NT and inhibin-A |
| 60 | 0.1 | 0.2 | 0.6 | 1.0 |
| 70 | 0.3 | 0.5 | 1.4 | 2.2 |
| 80 | 0.9 | 1.5 | 3.2 | 5.0 |
| 90 | 3.4 | 5.0 | 8.8 | 12.6 |

FIGS. 1 to 4 show the distributions of estimated risk of a term pregnancy with Down's syndrome in unaffected pregnancies and in Down's syndrome pregnancies using different markers in accordance with the present invention. In these figures, the vertical lines illustrate the detection rate (corresponding to the area under the Down's syndrome distribution curve to the right of the vertical line) achievable at a 5% false-positive rate (corresponding to the area under the unaffected distribution curve to the right of the vertical line). The dotted lines indicate uncertainties in the precise risk estimates.

FIG. 1 shows the distributions when using PAPP-A between 10 and 13 weeks and AFP, uE₃ and inhibin-A between 14 and 22 weeks.

Figure 2:
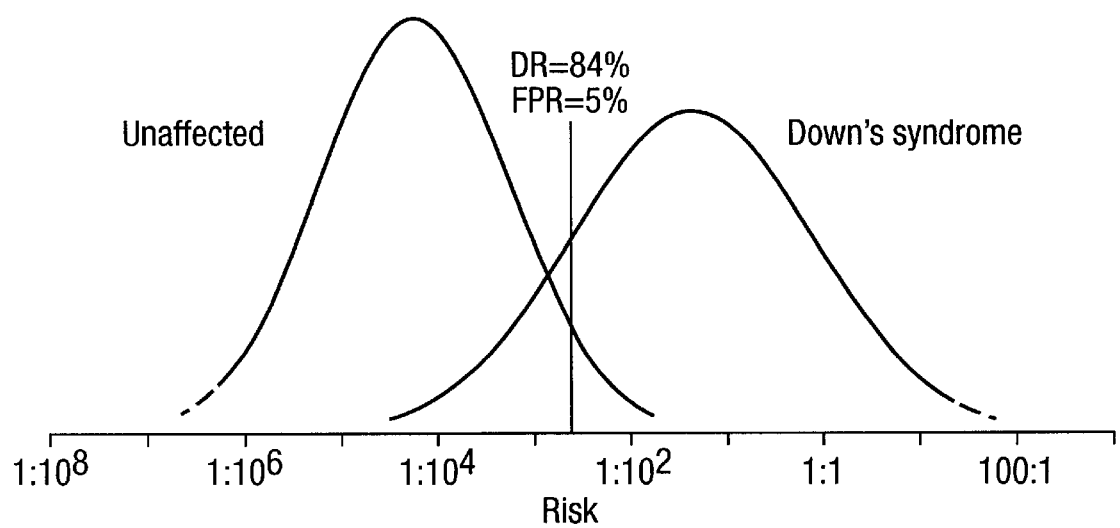

FIG. 2 shows the distributions when using PAPP-A and free β-hCG between 10 and 13 weeks and AFP, uE₃ and inhibin-A between 14 and 22 weeks.

Figure 3:
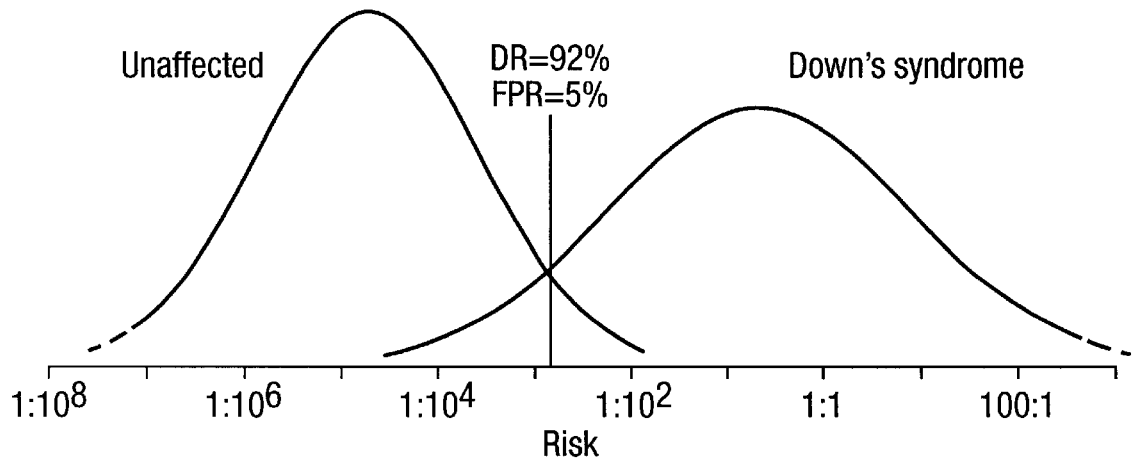

FIG. 3 shows the distributions when using NT and PAPP-A between 10 and 13 weeks and AFP, uE₃ inhibin A and total hCG between 14 and 22 weeks.

Figure 4:
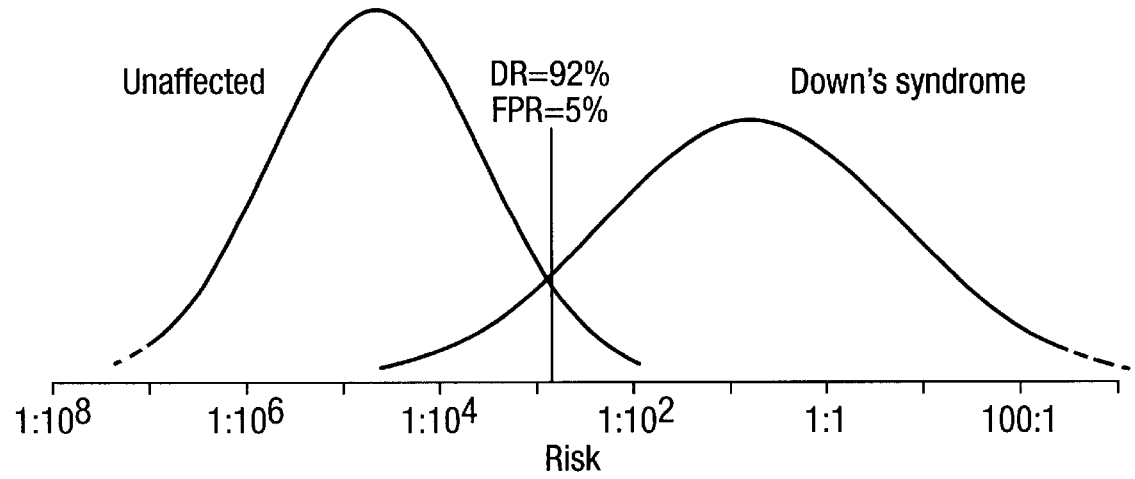
Figure 5:
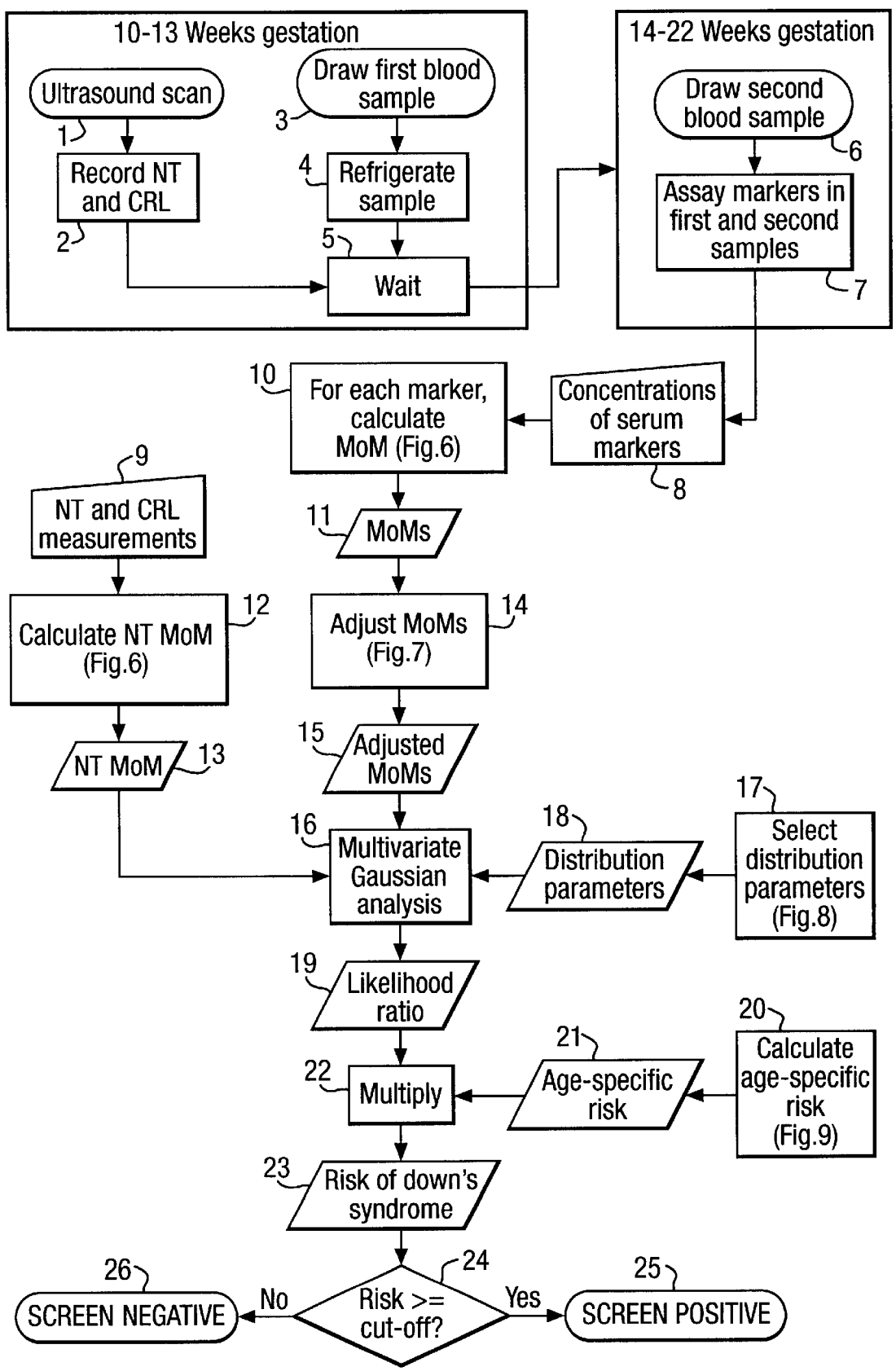
FIG. 5 is a flowchart illustrating a specific method according to the present invention, in particular, a screening test that involves deriving a risk estimate from measurements made on biochemical samples and/or ultrasound images collected at different stages of pregnancy.

FIG. 4 shows the distributions when using NT, PAPP-A and free β-hCG between 10 and 13 weeks and AFP, uE₃ and inhibin-A between 14 and 22 weeks.

As an alternative, a sequential test can be performed. In this case the risk is initially determined based on only the marker levels from the first stage of pregnancy. This first estimate of risk is compared with a predetermined cut-off risk as is known for initial classification as screen-positive or screen-negative. Women having a screen-positive result are referred for a diagnostic test and might not be tested for screening marker levels at the second stage of pregnancy.

Women initially classified as screen-negative are retested for markers measured at the second stage of pregnancy. The risk of Down's syndrome is determined again using one of two options.

As a first option, the markers from both the first and second stages of pregnancy are used. In determining the risk, the likelihood ratio can be calculated in the same way as in the non-sequential test described first above. Again it is desirable to take account of any correlation between the markers. As a refinement, the distributions of the screening markers used in determining the likelihood ratio arising from the combination of markers from the first and second stages of pregnancy are modified to allow for the fact that women with screen-positive results at the first stage of pregnancy have been removed from the sample presenting for the second test. The modified distributions of the markers measured at the second stage of pregnancy are typically derived by computer simulation.

The likelihood ratio computed in this way is then multiplied by the background risk, expressed as an odds ratio, after adjusting the background risk to take account of the fact that the women having a screen-positive result in the initial test at the first stage of pregnancy have been removed from the sample. The background risk can be reduced by multiplying the original background risk for the population by the complement of the overall detection rate of the test at the first stage of pregnancy, that is the detection rate expressed as a proportion. For more accuracy, one can allow for the fact that the detection rate and the false-positive rate of the test at the first stage of pregnancy vary with age. This is done by determining the detection rate and false-positive rate of the test carried out at the first stage of pregnancy for each age band (eg. a year of maternal age). The age-specific detection and false-positive rates are then used to determine the number of affected and unaffected pregnancies at each age in a simulated population presenting for the test at the second stage of pregnancy, and thereby the age-specific prevalence of Down's syndrome among these women.

The adjusted background risk is multiplied by the likelihood ratio to calculate the risk estimate. The estimated risk is classified as screen-positive or screen-negative based on a comparison with a predetermined cut-off. The appropriate cut-off level is selected to achieve an acceptable overall detection-rate and false-positive rate, taking into account the detection rate and false-positive rate of the first test. The overall detection rate and false-positive rate, can be estimated in the usual way for different cut-off levels, but using the residual age distributions of women with screen-negative results from the first test.

As a second but less effective option, the risk of Down's syndrome is calculated using the markers measured at the second stage of pregnancy, without considering the levels of markers measured at the first stage of pregnancy, but otherwise allowing for the effect of screening at the first stage by adjusting the background risk as described above.

For women classified as screen-negative in the first test, the alternative, sequential method increases the discriminatory power over tests carried out at a single stage of pregnancy. Such improvement is not achieved for the women classified as screen-positive in the first test because the screening marker levels from the second stage of pregnancy are not used. Whilst the overall benefit of the sequential test is not as great as the benefit of the non-sequential combined test first described, the sequential test may be better psychologically for the patients who receive an immediate result at the first stage of pregnancy without waiting until the second stage of pregnancy.

FIGS. 5 to 9 are flowcharts illustrating a specific method according to the present invention which is explained in detail below.

In the first trimester at around 8 to 13 weeks, or preferably around 10 to 13 weeks, an ultrasound scan is taken in step 1 and the nuchal translucency (NT) marker and the crown-rump length (CRL) are measured and recorded in step 2. At the same stage, a blood sample is drawn in step 3, and the separated serum is refrigerated in step 4, whereupon no action is taken during a wait in step 5 until after a second sample is drawn in the second trimester. The ultrasound scan 1 and the blood sample 3 may be performed as alternatives or together depending whether it is desired to use ultrasound markers, biochemical markers or both.

In the second trimester at around 14 to 22 weeks, a second blood sample is drawn in step 6. Subsequently in step 7, the first and second samples are assayed for the respective biochemical markers selected.

The processing of the measurements taken in steps 2 and 7 is described below and illustrated in the blocks numbered 8 and above in FIGS. 5 to 8. This processing may be implemented as logical operations in a data processing apparatus, suitably a general purpose computer appropriately programmed by a computer program of instructions to effect the logical operations by interconnected machine modules. Thus the blocks numbered 8 and above also illustrate elements of the computer program which performs the processing and the machine modules. In particular, the process blocks represent processing performed by the computer processor. The data entry blocks represent data entry processing which may be implemented by use of appropriate data entry fields shown on a display into which data may be entered from the computer's keyboard. The data item blocks represent stored reference data which may be stored in the memory of the computer in files referenced by the computer program.

Data input means are used to input the concentrations (levels) of the serum markers in step 8 and the NT marker level and CRL measurement in step 9. If the levels from the first trimester are input immediately after measurement a message may be automatically generated and displayed at an appropriate time in the second trimester to remind the user that measurements from a second sample are due.

In step 10, each marker level is re-expressed as a multiple of the median (MoM) level for unaffected pregnancies of the same gestational age and output as data item 11.

Figure 6:
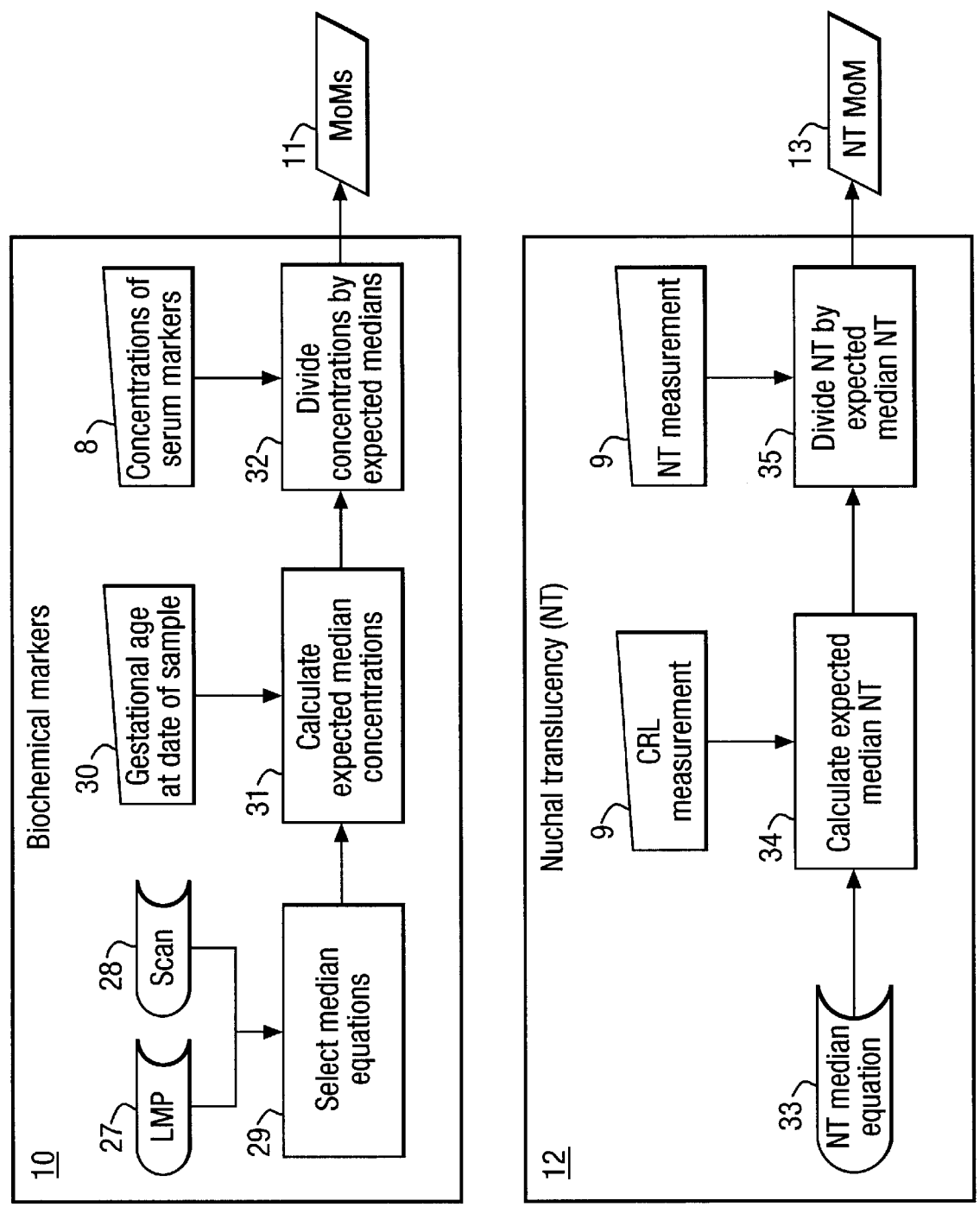
FIG. 6 is a flowchart illustrating the procedure for calculating multiples of the median (MoM) for biochemical and ultrasound markers.

Step 10 is illustrated in more detail in FIG. 6. Stored data LMP 27 and scan 28 specific to respective methods of estimating gestational age are used to select an equation which estimates the expected median concentrations for different gestational ages for each marker in step 29. Data LMP 27 is specific to estimation of gestational age based on the first day of the last menstrual period. Data scan 28 is specific to estimation of gestational age from an ultrasound measure of the fetus, usually a BPD or a CRL. The equations selected based on stored data 27 or 88 may be simple linear equations or may be more complicated. For example, in the case of inhibin A in the second trimester. Since inhibin-A levels decline at the start of the second trimester, and start to rise again after 17 weeks gestation, it is preferable to use a log-quadratic regression to calculate the median inhibin-A level at different gestational ages. The following equation is suggested in Watt H C, Wald N J, Huttly W J (1998); The pattern of maternal serum inhibin-A concentrations in the second trimester of pregnancy. Pregnat Diagn 18, 846–848:

$$\log_{10} I = k + 0.0001864 \times (a-120)^2$$

where I is the inhibin-A concentration, a is the gestational age in days and the coefficient k is separately derived for each screening centre.

Based on an input in step 30 of the gestational age at the date of the sample, for each marker in step 31 the expected median levels in unaffected pregnancies of the same gestational age is calculated using the equation selected in step 29. In step 32, each marker level input in step 8 is divided by the expected median for that marker to output the MoM as data item 11.

In step 12, the NT marker is re-expressed as a MoM and output as data item 13. The specific calculation of step 12 is illustrated in FIG. 6 and corresponds to the MoM calculation for the biochemical markers, except that the CRL measurement input in step 9 is used as the estimate of gestational age. Stored data 33 represents the NT medians for different CRL measurements, preferably as an equation.

There can be considerable systematic variation in nuchal translucency (NT) measurements from one ultrasonographer to another. Therefore, the stored data 33 may, optionally, represent NT medians which are ultrasonographer-specific in cases where it has been possible to base this data on sufficiently large numbers of measurements taken by individual ultrasonographers. In step 34 stored data 33 is used to calculate the expected median NT levels in unaffected pregnancies of the same CRL, i.e. the same age. In step 35, the NT measurement input in step 9 is divided by the expected median NT to give the NT MoM which is output as data item 13.

Figure 7:
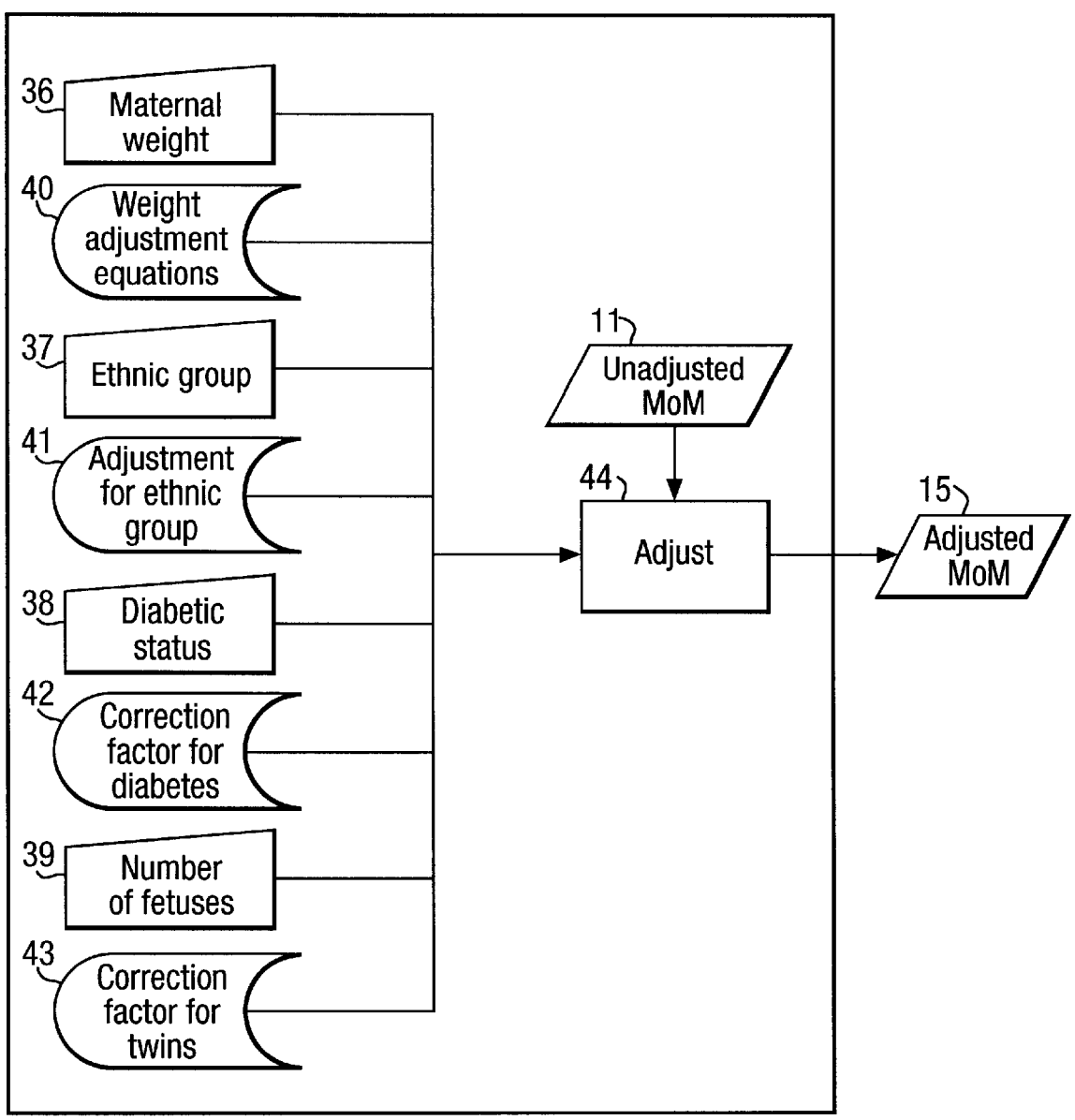
FIG. 7 is a flowchart illustrating the procedure for adjusting MoM values to allow for various factors, other than gestational age, that may affect biochemical marker levels.
Figure 8:
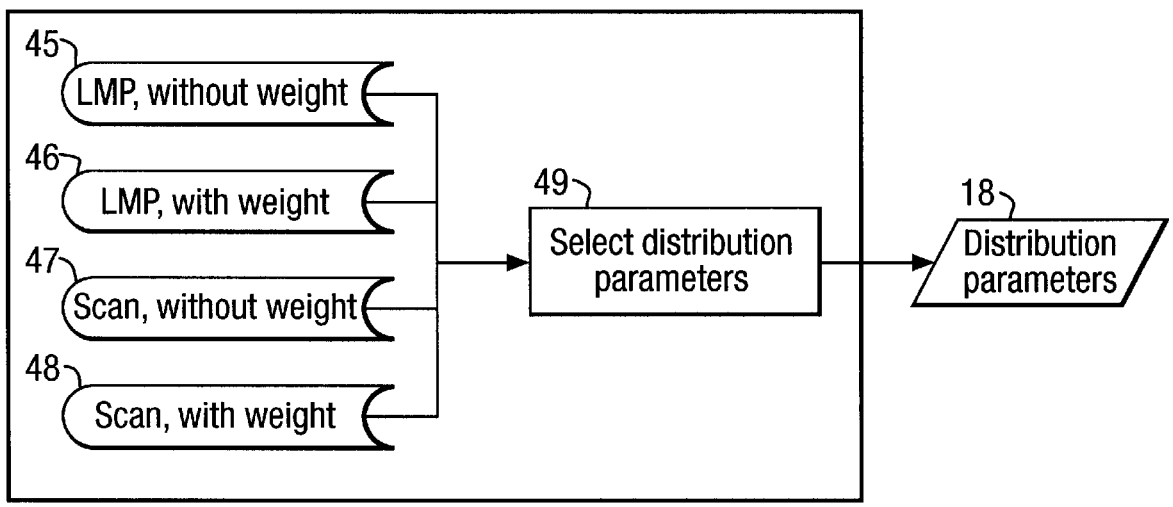
FIG. 8 is a flowchart illustrating the procedure for selecting the appropriate parameters of the distributions of screening markers in affected and unaffected pregnancies.
Figure 9:
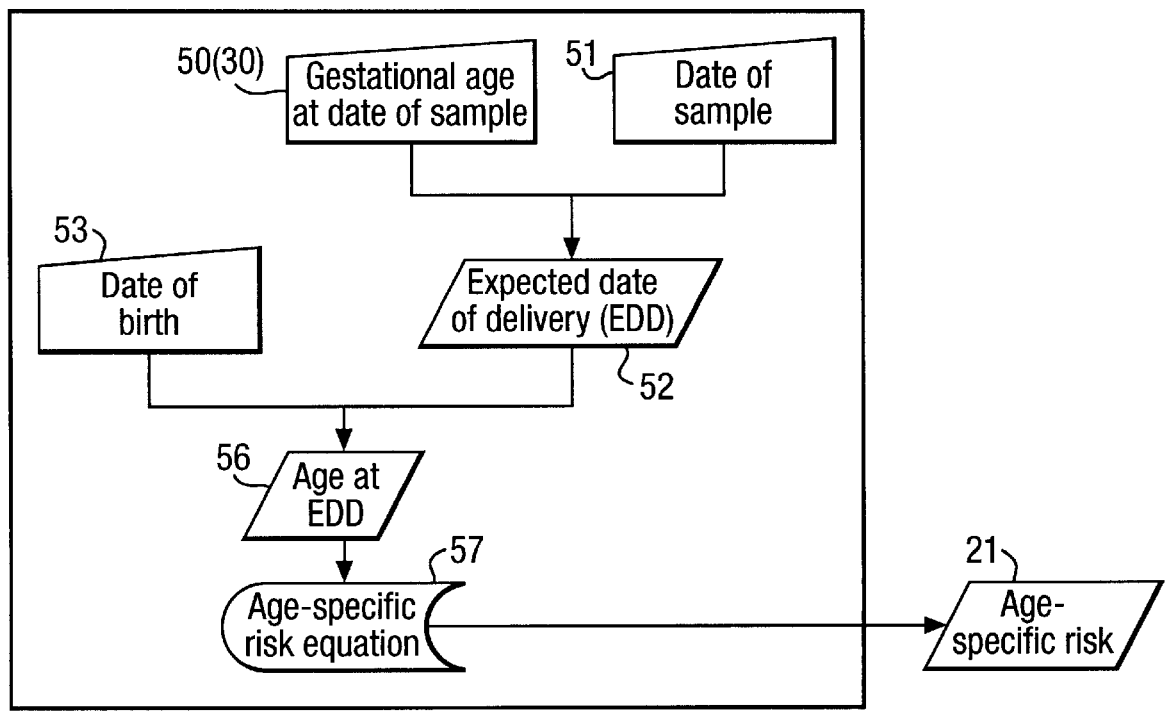
FIG. 9 is a flowchart illustrating the procedure for calculating the age-specific risk of Down's syndrome.

Optionally, the MoMs 11 for the biochemical markers may be adjusted in step 14 which is illustrated in detail in FIG. 7. Based on an input of any one or more of maternal weight, ethnic group, diabetic status and the number of fetuses in steps 36 to 39, respectively, stored weight adjustment equations 40, ethnic group adjustments 41, diabetes correction factors 42 and multiple birth correction factors 43 are used in step 44 to adjust the MoMs 11. The adjusted MoMs are output as data item 15.

In step 16, a multivariate Gaussian analysis of the MoM for all the markers from each stage of pregnancy is performed. For use in this analysis, distribution parameters 18 are selected in step 17 which is described in more detail in FIG. 8. For each marker the distribution parameters are stored as reference data 45 to 48 for different methods of estimating gestational age (LMP or scan) and based on whether or not the MoM has been adjusted for maternal weight. In step 49, the appropriate distribution parameters are selected and output as data item 18.

The multivariate Gaussian analysis 16 outputs a likelihood ratio as data item 19. This needs to be multiplied by a background risk to derive the estimated risk of Down's syndrome. Whilst an overall population risk may be used, the present method uses age-specific risks calculated in step 20 which is described in more detail in FIG. 9. The gestational age of the sample input in step 50 (or 30) and the date of the sample input in step 51 are used to calculate the expected date of delivery (EDD) in step 52. The maternal date of birth is input in step 53 and is combined with the EDD to calculate the age at EDD as data item 56. This is used in the stored age-specific risk equation 57 to output the age-specific risk as data item 21. The likelihood ratio 19 and age-specific risk 21 are multiplied in step 22 to output the estimated risk of Down's syndrome as data item 23. The estimated risk 23 is compared with a predetermined cut-off in step 24 to produce a screen-positive result 25 when the risk is equal to or greater than the cut-off, or a screen-negative result 26 otherwise.

The apparatus may be arranged to provide estimates of the expected screening performance (i.e. the detection rate, false-positive rate and odds of being affected given a positive result), taking into account the age distribution of the screened population, the combination of screening markers used, the risk cut-off used, and other factors. The performance observed in practice can then be compared to the expected performance as an aid to monitoring.

The values of the stored data used in the method described above depends on which markers from the two stages of pregnancy are selected to be used. Appropriate data values for each marker are known, for example from the references.

What is claimed is:

1. A method of determining whether a pregnant woman is at an increased risk of having a fetus with Down's syndrome, the method comprising the steps of:

measuring the level of at least one screening marker from a first trimester of pregnancy by:
   (i) assaying a sample obtained from the pregnant woman at said first trimester of pregnancy for at least one first biochemical screening marker; and/or
   (ii) measuring at least one first ultrasound screening marker from an ultrasound scan taken at said first trimester of pregnancy;

measuring the level of at least one second screening marker from a second trimester of pregnancy, the at least one second screening marker from the second trimester of pregnancy being different from the at least one first screening marker from the first trimester of pregnancy, by:
   (i) assaying a sample obtained from the pregnant woman at said second trimester of pregnancy for at least one second biochemical screening marker; and/or
   (ii) measuring at least one second ultrasound screening marker from an ultrasound scan taken at said second trimester of pregnancy; and determining the risk of Down's syndrome by comparing the measured levels of both the at least one first screening marker from the first trimester of pregnancy and the at least one second screening marker from the second trimester of pregnancy with observed relative frequency distributions of marker levels in Down's syndrome pregnancies and in unaffected pregnancies.

2. A method according to claim 1, wherein the step of determining the risk of Down's syndrome comprises deriving the likelihood ratio of Down's syndrome using a multivariate analysis of the measured levels of the screening markers from both the first and second trimesters of pregnancy based on distribution parameters derived from a set of reference data.

3. A method according to claim 2, wherein said multivariate analysis is a multivariate Gaussian analysis.

4. A method according to claim 2, wherein the step of determining the risk of Down's syndrome further comprises multiplying the likelihood ratio by an age-specific risk.

5. A method according to claim 1, further comprising the step of re-expressing each measured level of a screening marker as a multiple of the median level of the respective screening marker in unaffected pregnancies of the same gestational age as the fetus of the pregnant woman.

6. A method according to claim 1, further comprising comparing the determined risk with a predetermined cut-off level to classify the pregnant women as screen-positive or screen negative based on the comparison.

7. A method according to claim 1, wherein said step of measuring the level of at least one first screening marker from a first trimester of pregnancy includes assaying a serum sample obtained from the pregnant woman during said first trimester of pregnancy for one selected from the group of PAPP-A, free β-hCG and both.

8. A method according to claim 7, wherein said step of measuring the level of at least one second screening marker from a second trimester of pregnancy includes assaying a serum sample obtained from the pregnant woman during said second trimester of pregnancy for one selected from the group of AFP, $uE_3$, inhibin-A, free β-hCG, free α-hCG, total hCG and combinations thereof.

9. A method according to claim 7, wherein said step of measuring the level of at least one second screening marker from a second trimester of pregnancy includes assaying a urine sample obtained from the pregnant woman during said second trimester of pregnancy for one selected from the group of β-core hCG, total oestriol and both.

10. A method according to claim 1, wherein said step of measuring the level of at least one first or second screening marker from a first or a second trimester of pregnancy includes assaying a sample of cells obtained from the pregnant woman during said first or second trimester of pregnancy.

11. A method according to claim 1, further comprising adjusting any or all of the measured levels of the screening markers to allow for one or more factors selected from the group of maternal race, maternal weight, multiple birth and diabetic status.

12. A method according to claim 1, further comprising the steps of:
obtaining said sample from the pregnant woman during said first trimester of pregnancy and/or taking said ultrasound scan during said first trimester of pregnancy; and
obtaining said sample from the pregnant woman during said second trimester of pregnancy and/or taking said ultrasound scan during said second trimester of pregnancy.

13. A method according to claim 1, further comprising the steps of:
obtaining a first sample from the pregnant woman during said first trimester of pregnancy;
storing the first sample under refrigeration; and
obtaining a second sample from the pregnant woman during said second trimester of pregnancy,
wherein the first and second samples are assayed at the same time.

14. A method according to claim 1, further comprising measuring the level of at least one further screening marker from at least one further stage of pregnancy and additionally comparing the measured level of said at least one further screening marker with observed relative frequency distributions of marker levels in Down's syndrome pregnancies and in unaffected pregnancies in determining the risk of Down's syndrome.

15. A method according to claim 1, further comprising:
determining a first risk estimate of Down's syndrome using the measured level of the at least one first screening marker from the first trimester of pregnancy;
comparing the first risk estimate with a predetermined cut-off level to initially classify the pregnant woman as screen-positive or screen-negative based on the comparison; and
performing said steps of measuring the level of at least one second screening marker from a second trimester of pregnancy and determining the risk of Down's syndrome using the measured levels of the screening markers from both the first and second trimesters of pregnancy if the pregnant woman is initially classified as screen-negative.

16. A method according to claim 15, wherein said step of determining the risk of Down's syndrome comprises calculating a likelihood ratio and multiplying by an age-specific risk which is adjusted, relative to the original age-specific risk of the original population presenting for the test during the first trimester of pregnancy, to allow for fact that the proportion of affected pregnancies initially classified as screen-positive have been removed from the sample presenting for the test during the second trimester of pregnancy.

17. A method according to claim 15, wherein said step of determining the risk of Down's syndrome comprises calculating a likelihood ratio and multiplying by an age-specific risk which is adjusted, relative to the original age-specific risk of the original population presenting for the test during the first trimester of pregnancy, to allow for the fact that the age-specific proportions of affected and unaffected pregnancies initially classified as screen-positive have been removed from the sample presenting for the test during the second trimester of the pregnancy.

18. A method according to claim 15, wherein said step of determining the risk of Down's syndrome comprises calculating a likelihood ratio based on distributions of the levels of markers which are modified, relative to the original distributions of the levels of markers of the original population presenting for the test during the first trimester of pregnancy, to allow for the fact that women initially classified as screen-positive have been removed from the sample presenting for the test during the second trimester of pregnancy.

19. A method according to claim 15, further comprising comparing the determined risk with a second predetermined cut-off level to classify the pregnant woman as screen-positive or screen negative based on the comparison, wherein said second cut-off level is determined based on the residual age distribution of pregnant women initially classified as screen-negative.

20. A method of determining whether a pregnant woman is at an increased risk of having a fetus with Down's syndrome, the method comprising the steps of:
measuring the level of at least one first screening marker from a first trimester of pregnancy by:
(i) assaying a sample obtained from the pregnant woman at said first trimester of pregnancy for at least one first biochemical screening marker; and/or
(ii) measuring at least one first ultrasound screening marker from an ultrasound scan taken at said first trimester of pregnancy;
determining a first risk estimate of Down's syndrome by comparing the measured level of the at least one first screening marker level from the first trimester of pregnancy with observed relative frequency distributions of marker levels in Down's syndrome pregnancies and in unaffected pregnancies;
comparing the first risk estimate with a predetermined cut-off level to initially classify the pregnant woman as screen-positive or screen-negative based on the comparison; and
if the pregnant woman is initially classified as screen-negative:
measuring the level of at least one second screening marker from a second trimester of pregnancy, the at least one second screening marker from the second trimester of pregnancy being different from the at least one first screening marker from the first trimester of pregnancy, by:
(i) assaying a sample obtained from the pregnant woman during said second trimester of pregnancy for at least one second biochemical screening marker; and/or
(ii) measuring at least one second ultrasound screening marker from an ultrasound scan taken during said second trimester of pregnancy; and
determining the risk of Down's syndrome by comparing the measured level of both the at least one first screening marker from the first trimester of pregnancy and the at least one second screening marker from second trimester of pregnancy with observed relative frequency distributions of marker levels in Down's syndrome pregnancies and in unaffected pregnancies.

21. A method according to claim 20, wherein said step of determining the risk of Down's syndrome comprises calculating a likelihood ratio and multiplying by an age-specific risk which is adjusted, relative to the original age-specific risk of the original population presenting for the test during the first trimester of pregnancy, to allow for fact that the proportion of affected pregnancies initially classified as screen-positive have been removed from the sample presenting for the test during the second trimester of pregnancy.

22. A method according to claim 20, wherein said step of determining the risk of Down's syndrome comprises calculating a likelihood ratio and multiplying by an age-specific risk which is adjusted, relative to the original age-specific risk of the original population presenting for the test during the first trimester of pregnancy, to allow for the fact that the age-specific proportions of affected and unaffected pregnancies initially classified as screen-positive have been removed from the sample presenting for the test during the second trimester of the pregnancy.

23. A method according to claim 20, wherein said step of determining the risk of Down's syndrome comprises calculating a likelihood ratio based on distributions of the levels of markers which are modified, relative to the original distributions of the markers of the original population presenting for the test during the first trimester of pregnancy, to allow for the fact that women initially classified as screen-positive have been removed from the sample presenting for the test during the second trimester of pregnancy.

24. A method according to claim 20, further comprising comparing the determined risk with a second predetermined cut-off level to classify the pregnant woman as screen-positive or screen negative based on the comparison wherein said second-mentioned cut-off level is determined based on the residual age distribution of pregnant women initially classified as screen-negative.

\* \* \* \* \*